US010189793B1

(12) United States Patent
Yang et al.

(10) Patent No.: US 10,189,793 B1
(45) Date of Patent: Jan. 29, 2019

(54) METHOD FOR PREPARING AZOXYSTROBIN

(71) Applicant: CAC Nantong Chemical Co., LTD, Nantong (CN)

(72) Inventors: Binglian Yang, Shanghai (CN); Haishui Wang, Shanghai (CN); Simian Xie, Shanghai (CN); Xiaohong Tian, Shanghai (CN); Jiwang Xu, Nantong (CN)

(73) Assignee: CAC NANTONG CHEMICAL CO., LTD, Nantong (CN)

( * ) Notice: Subject to any disclaimer, the term of this patent is extended or adjusted under 35 U.S.C. 154(b) by 0 days.

(21) Appl. No.: 15/869,205

(22) Filed: Jan. 12, 2018

(30) Foreign Application Priority Data

Oct. 31, 2017 (CN) .......................... 2017 1 1049391

(51) Int. Cl.
*C07D 239/52* (2006.01)

(52) U.S. Cl.
CPC .................................. *C07D 239/52* (2013.01)

(58) Field of Classification Search
CPC .................................................... C07D 239/52
See application file for complete search history.

(56) References Cited

U.S. PATENT DOCUMENTS 5,849,910 A 12/1998 Kameswaran

FOREIGN PATENT DOCUMENTS

| | | | |
|---|---|---|---|
| CN | 101163682 | A | 4/2008 |
| EP | 0794177 | A1 | 9/1997 |
| WO | 2006114572 | A2 | 11/2006 |
| WO | 2008043977 | A1 | 4/2008 |

OTHER PUBLICATIONS

European Search Report issued in Application No. 18155233.2 dated Apr. 26, 2018.

*Primary Examiner* — Emily A Bernhardt

(74) *Attorney, Agent, or Firm* — Dilworth IP, LLC

(57) ABSTRACT

The present invention provides a process for preparing azoxystrobin, which is performed by reacting 2-cyanophenol or a salt thereof with a compound represented by formula I under the catalysis of a trimethylamine catalyst to obtain the azoxystrobin represented by formula II, which allows the yield of the product azoxystrobin to reach 98% or more, the yield of separated product to reach 95% or more and the post-processing to be simple. The trimethylamine catalyst can be recycled and reused in synthesizing the target product azoxystrobin, which not only reduces the cost but also reduces the total nitrogen and COD in wastewater. The advantages regarding of cost and environmental protection of the method according to the present invention are significant and thus the method is suitable for industrial production.

16 Claims, No Drawings

METHOD FOR PREPARING AZOXYSTROBIN

TECHNICAL FIELD

The present invention belongs to the technical field of organic synthesis and relates to a method for preparing azoxystrobin.

BACKGROUND OF THE INVENTION

Azoxystrobin is a novel, high-efficient, broad-spectrum, systemic fungicide that can be used for spraying on stems and leaves, and seed processing as well as soil processing. However, there exist some problems in the synthesis of azoxystrobin including, for example, the impossibility of catalyst recycling, the high costs, the difficulties in post-processing and the low yields, which affect the application of azoxystrobin.

CN101163682 discloses a method for preparing azoxystrobin by reacting 2-cyanophenol with a compound represented by formula (I) under the catalysis of DABCO. The amount of DABCO used in this method is 0.1-2% in mole relative to the compound represented by formula (I) and the compound represented by formula (I) has a structure of

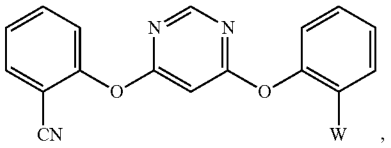

, wherein w is methyl (E)-2-(3-methoxy) acrylate group, i.e. $C(CO_2CH_3)$=$CHOCH_3$, or methyl 2-(3,3-dimethoxy) propionate group, i.e. $C(CO_2CH_3)CH(OCH_3)_2$, or a mixture of the two groups. In this method, the reaction yield can reach 98.7% with the catalyst DABCO in a polar aprotic solvent DMF having a high boiling point (150° C.). During post-processing, the DMF is firstly removed by vacuum distillation and then toluene and water are added and stirred until stratification, to provide a toluene solution containing azoxystrobin. Most of the catalyst comes into wastewater due to the good water solubility of DABCO and the catalyst DABCO cannot be recycled due to its high boiling point (174° C.), resulting in increased costs and high total nitrogen and COD in wastewater, which are difficult to process. During the post-processing of this method, there is a need for high vacuum distillation (to remove DMF at 100° C.), which increases the difficulties in workshop operation, as well as a need for subsequent addition of toluene and water, which causes a cumbersome operation.

In addition, EP0794177 discloses a method for synthesizing an asymmetric 4,6-disubstituted pyrimidine by reacting a substituted chloropyrimidine compound with trimethylamine to form a substituted pyrimidine halogenated quaternary ammonium salt, in which the amount of trimethylamine is 3 times more than that of the substituted chloropyrimidine. The substituted pyrimidine halogenated quaternary ammonium salt is separated and subjected to a reaction with a phenolic compound in an organic solvent to prepare an asymmetric, 4,6-disubstituted pyrimidine compound. The amount of trimethylamine used in this method is large; and the obtained quaternary ammonium salt needs to be separated, and the separation yield is low, only about 80%; in addition, two steps are needed to obtain 4,6-disubstituted pyrimidine compound, which causes a cumbersome industrial operation.

Therefore, such a method for preparing azoxystrobin is desired in the art that in this method the catalyst can be recycled, the total nitrogen and COD in wastewater are reduced and a "one-pot synthesis" can be achieved, and the method is convenient for industrial operation, has the advantages of environmental protection and high yield.

SUMMARY OF THE INVENTION

In view of the deficiencies of the prior art, the object of the present invention is to provide a method for preparing azoxystrobin, which overcomes the problems in the prior art including the impossibility of catalyst recycling, the high cost, the difficulties in recycling, and the cumbersome industrial process. The catalyst is easily recycled, the product yield is high, and a "one-pot synthesis" is achieved in the technical scheme of the present invention, and it is convenient for industrial application.

The following technical solutions are adopted by the present invention to achieve the object.

The present invention provides a method for preparing azoxystrobin, comprising: reacting 2-cyanophenol or a salt thereof with a compound represented by formula I under the catalysis of a trimethylamine catalyst to obtain azoxystrobin represented by formula II:

Formula I

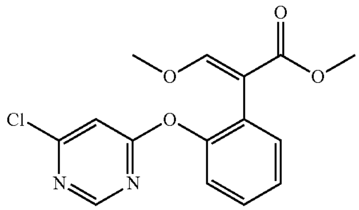

Formula II

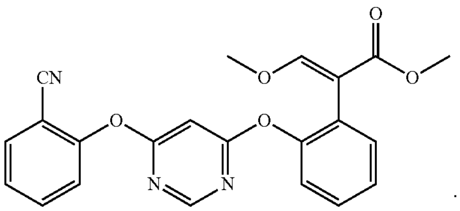

.

The present invention provides a method for preparing azoxystrobin, which is performed by using a trimethylamine catalyst for catalyzing, allowing 2-cyanophenol or a salt thereof to be reacted with a compound represented by formula I to obtain azoxystrobin and allowing the yield of the product azoxystrobin to reach 98% or more and the post-processing to be simple. The trimethylamine catalyst can be recycled and reused in synthesizing the target product azoxystrobin, which not only reduces the cost but also reduces the total nitrogen and COD in wastewater. The advantages regarding of cost and environmental protection in the method according to the present invention are significant and thus the method is suitable for industrial production.

Preferably, the trimethylamine catalyst is trimethylamine, a trimethylamine solution, or a salt of trimethylamine. That is, in the present invention, the trimethylamine can be pure trimethylamine (i.e. trimethylamine which is in the form of gas at normal temperature and pressure), and can also be a trimethylamine solution or a salt forming from trimethylamine.

Preferably, the trimethylamine solution is any one selected from the group consisting of a trimethylamine solution in water, a trimethylamine solution in methanol, a trimethylamine solution in ethanol, a trimethylamine solution in toluene and a trimethylamine solution in xylene, or a combination of at least two selected therefrom.

In the present invention, the concentration of the trimethylamine solution used is 10-60%, for example 10%, 12%, 15%, 18%, 20%, 25%, 30%, 35%, 40%, 45%, 50%, 55% or 60%, preferably 20-33%. The trimethylamine solutions are commercially available products or can be prepared by processing trimethylamine gas.

Preferably, the salt of trimethylamine is any one selected from the group consisting of trimethylamine hydrochloride, trimethylamine sulfate and trimethylamine methanesulfonate, or a combination of at least two selected therefrom, and may also be a trimethylamine hydrochloride solution in water. Wherein, the content of trimethylamine hydrochloride is 98%, which is commercially available industrial product or customized, the concentration of the trimethylamine hydrochloride solution in water is 15% or more.

The reaction is performed in a non-polar inert solvent; preferably, the non-polar inert solvent is toluene, xylene or butyl acetate, preferably toluene.

The reaction of the present invention is performed under the catalysis of trimethylamine and in a non-polar inert solvent. When the reaction is completed, water is added directly. Layers are separated to obtain an organic phase containing azoxystrobin, and the measured reaction yield can reach 98% or more. An azoxystrobin crude product is obtained by desolvation, then methanol and water are added to crystallize to provide the final product with a yield of 95% or more and a product content of 98% or more. Surprisingly, the solvent used in the reaction and the solvent used in the post-processing of the present invention can be selected as the same solvent, which omits a desolvation process under high vacuum, saves equipments and operating time, is convenient for production application and improves production efficiency without affecting the yield.

In the present invention, the salt of 2-cyanophenol is potassium 2-cyanophenoxide, and both the 2-cyanophenol and the potassium 2-cyanophenoxide may be commercially available products.

In the present invention, the reaction should be performed in the presence of an acid acceptor, and the suitable acid acceptor is potassium carbonate and/or sodium carbonate. The acid acceptor is present so that the trimethylamine catalyst does not react with hydrochloric acid and remains in a free state, maintaining the catalytic activity until the reaction is completed.

In the present invention, the reaction has the equation as following:

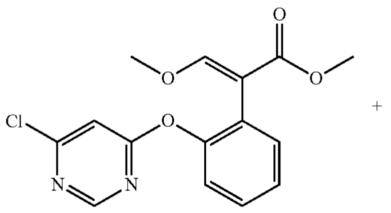

-continued

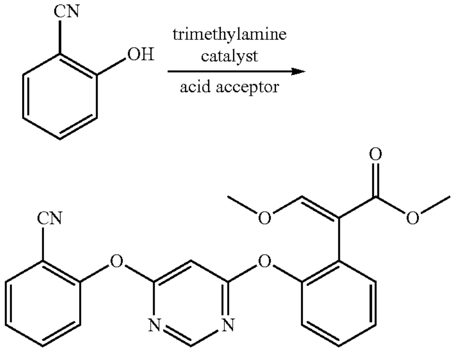

In the present invention, the chemical name of the compound represented by formula I may be methyl (E)-2-[2-[6-chloropyrimidin-4-yloxy]phenyl]-3-methoxyacrylate.

In the present invention, the amount of the trimethylamine catalyst is 0.5-15 mol %, for example 0.5 mol %, 0.6 mol %, 0.8 mol %, 1 mol %, 3 mol %, 5 mol %, 7 mol %, 9 mol %, 10 mol %, 12 mol % or 15 mol % of the compound represented by formula I.

Preferably, the molar ratio of 2-cyanophenol or a salt thereof to the compound represented by formula I is (1-1.5):1, for example 1:1, 1.1:1, 1.2:1, 1.3:1, 1.4:1 or 1.5:1, etc., preferably (1-1.2):1.

Preferably, the molar ratio of the acid acceptor to the compound represented by formula I is (0.6-2):1, for example 0.6:1, 0.7:1, 0.8:1, 0.9:1, 1:1, 1.2:1, 1.4:1, 1.6:1, 1.8:1 or 2:1, etc., preferably (0.7-1):1.

Preferably, the reaction is performed at a temperature of 50-120° C., for example 50° C., 60° C., 70° C., 80° C., 90° C., 100° C., 110° C. or 120° C., etc.

Preferably, the reaction is performed for 5-20 h, for example 5 h, 8 h, 10 h, 12 h, 14 h, 16 h, 18 h or 20 h.

As a preferred technical solution of the present invention, the method for preparing azoxystrobin specifically comprises the following steps of:

reacting 2-cyanophenol or a salt thereof with a compound represented by formula I in a non-polar inert solvent at 50-120° C. under the catalysis of a trimethylamine catalyst to obtain the azoxystrobin represented by formula II, wherein the molar ratio of 2-cyanophenol or a salt thereof to the compound represented by formula I is (1-1.5):1, the molar ratio of the acid acceptor to the compound represented by formula I is (0.6-2): 1, and the amount of the trimethylamine catalyst is 0.5-15 mol % of the compound represented by formula I;

adding water directly to wash, desolventizing to obtain a crude product and then crystallizing the solvent to provide an azoxystrobin product during the post-processing.

In the present invention, the trimethylamine catalyst can be recycled. Most surprisingly, the trimethylamine catalyst (boiling point being 2.9° C.) can be recycled by multistage absorption recycling techniques with ammonia or amine-based gas which are well-known to those skilled in the art. The wastewater which is separated in the synthesis of azoxystrobin is collected and subjected to vacuum, azeotropic distillation or purged with an inert gas such as nitrogen to provide a gas mixture. The gas mixture is subjected to a multistage absorption with water, 15-25% aqueous hydrochloric acid solution, methanol or ethanol to obtain a trimethylamine solution in water, methanol or ethanol with a concentration up to 10-30%. The trimethylamine thus can be recycled with a recycling rate of 90% or more, which meets the synthesis of the azoxystrobin product, greatly reduces the total nitrogen and COD in water, and reduces the pressure of environmental protection.

The cost is reduced in the present invention by catalyzing the reaction with the trimethylamine catalyst. For example, the amount of DABCO catalyst, which is used in the synthesis of azoxystrobin in the prior art, is 0.1-2%. However, the price of DABCO is high, and the price of industrial products with a concentration of 100% is up to 60,000-70,000 Yuan/ton (market price in October 2017), while the price of trimethylamine with a concentration of 100%, which is a commonly used chemical, is 8,000 to 9,000 Yuan/ton (market price in October 2017). The amount of trimethylamine used in the present invention is within the range of catalyst (that is, 0.5-15 mol % of the raw materials). Although the amount of trimethylamine used is higher than that of DABCO, the molecular weight of trimethylamine (molecular weight being 59.11) is smaller than that of DABCO (molecular weight being 112.17), resulting that the actual amount of trimethylamine used is only 3-4 fold of that of DABCO. Therefore, the cost of the trimethylamine catalyst is less than 50% of DABCO catalyst required in synthesizing one ton of azoxystrobin product. In addition, the recycling rate of trimethylamine can reach 90% or more in the present invention. The catalyst cost of the present invention is significantly reduced compared to the prior art.

In the present invention, the recycled trimethylamine catalyst can be reused in synthesizing the target product azoxystrobin, which not only reduces the cost but also reduces the ammoniacal nitrogen and the COD content in wastewater, and remains a good catalytic effect, providing an azoxystrobin product with a high yield.

Compared with the prior art, the present invention has the following benefits:

The present invention provides a method for preparing azoxystrobin, which is performed by using a trimethylamine catalyst for catalyzing, allowing 2-cyanophenol or a salt thereof to be reacted with a compound represented by formula I to obtain azoxystrobin and allowing the reaction yield of the product azoxystrobin to reach 98% or more and the post-processing to be simple. The trimethylamine catalyst can be recycled to reuse for the synthesis of the target product azoxystrobin, which not only reduces the cost but also reduces the ammoniacal nitrogen and COD content in wastewater. The advantages regarding of cost and environmental protection in the method according to the present invention are significant and thus the method is suitable for industrial production.

DETAILED DESCRIPTION OF THE INVENTION

The technical solutions of the present invention are further described below by using specific embodiments. It should be understood by those skilled in the art that the examples are merely to help understand the present invention and should not be construed as specific limitations to the present invention.

The contents of the raw materials or products are represented by mass percentages in the following examples and the abbreviations of the raw materials involved refer to the following chemical names:

DBU: 1,8-diazabicyclo[5.4.0]undec-7-ene

DMAP: 4-dimethylaminopyridine.

Example 1

In this example, a trimethylamine solution in water with the amount of 8 mol % of methyl (E)-2-[2-[6-chloropyrimidin-4-yloxy]phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 3.58 g (0.02 mol, having a concentration of 33%) of trimethylamine solution in water were added sequentially into a 500 mL reaction flask, stirred, heated to 80° C. and incubated for 8 h. When the reaction was completed, 100 g of water was added. Layers were separated to obtain 253.59 g of a toluene solution of azoxystrobin, with a content of 40.21% (w/w), which is 98.9% of the theoretical value.

The toluene solution of azoxystrobin described above was distilled under reduced pressure. Distillation was stopped when the temperature in the reaction flask was 110° C., and then the temperature was reduced to 70° C. 70 g of methanol and 5 g of water were added and stirred. The temperature was held at 70-80° C. for 1 h, and then slowly reduced to 0-5° C., holding for 2 h. The mixture was filtered, washed twice with cold methanol (10 g×2) and dried to obtain 98.72 g of azoxystrobin as a white solid with a content of 98.21% and a yield of 96.14%.

The resulting product was characterized by NMR, the structure was characterized as follow: $^1$H NMR (400 MHz, $CDCl_3$): δ 3.61 (s, 3H, $OCH_3$), δ 3.77 (s, 3H, $OCH_3$), δ 6.44 (s, 1H, Py-H), δ 7.24-7.45 (m, 6H, Ar—H), δ 7.51 (s, 1H, C═CH), δ 7.67-7.74 (m, 2H, Ar—H), 8.42 (s, 1H, Py-H).

Example 2

In this example, a trimethylamine solution in water with the amount of 15 mol % of methyl (E)-2-[2-[6-chloropyrimidin-4-yloxy]phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 8.96 g (0.0375 mol, having a concentration of 33%) of trimethylamine solution in water were added sequentially into a 500 mL reaction flask, stirred, heated to 80° C. and incubated for 4 h. When the reaction was completed, 100 g of water was added. Layers were separated to obtain 247.34 g of a toluene solution of azoxystrobin, with a content of 41.21% (w/w), which is 98.94% of the theoretical value.

The post-processing was performed as Example 1 to provide 98.92 g of azoxystrobin with a content of 98.43% and a yield of 96.55%.

Example 3

In this example, a trimethylamine solution in water with the amount of 8 mol % of methyl (E)-2-[2-[6-chloropyrimidin-4-yloxy]phenyl]-3-methoxyacrylate was used as a catalyst and potassium 2-cyanophenoxide was used as a raw material to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 43.67 g (0.275 mol, 99%) of potassium 2-cyanophenoxide, 8.63 g (0.025 mol, having a concentration of 40%) of potassium carbonate solution in water and 3.58 g (0.02 mol, having a concentration of 33%) of trimethylamine solution in water were added sequentially into a 500 mL reaction flask, stirred, heated to 80° C. and incubated for 10 h. When the reaction was completed, 100 g of water was added. Layers were separated to obtain 247.16 g of a toluene solution of azoxystrobin, with a content of 41.24% (w/w), which is 98.94% of the theoretical value.

The post-processing was performed as Example 1 to provide 98.68 g of azoxystrobin with a content of 98.23% and a yield of 96.12%.

Example 4

In this example, a trimethylamine solution in methanol with the amount of 8 mol % of methyl (E)-2-[2-[6-chloropyrimidin-4-yloxy]phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 3.58 g (0.02 mol, having a concentration of 33%) of trimethylamine solution in methanol were added sequentially into a 500 mL reaction flask, stirred, heated to 80° C. and incubated for 8 h. When the reaction was completed, 100 g of water was added. Layers were separated to obtain 249.90 g of a toluene solution of azoxystrobin, with a content of 40.97% (w/w), which is 98.5% of the theoretical value.

The post-processing was performed as Example 1 to provide 98.49 g of azoxystrobin with a content of 98.16% and a yield of 95.87%.

Example 5

In this example, a trimethylamine hydrochloride with the amount of 8 mol % of methyl (E)-2-[2-[6-chloropyrimidin-4-yloxy]phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 1.95 g (0.02 mol, having a content of 98%) of trimethylamine hydrochloride were added sequentially into a 500 mL reaction flask, stirred, heated to 80° C. and incubated for 8 h. When the reaction was completed, 100 g of water was added. Layers were separated to obtain 250.61 g of a toluene solution of azoxystrobin, with a content of 41.02% (w/w), which is 98.10% of the theoretical value.

The post-processing was performed as Example 1 to provide 97.90 g of azoxystrobin with a content of 98.25% and a yield of 95.38%.

Example 6

In this example, a trimethylamine solution in water with the amount of 0.5 mol % of methyl (E)-2-[2-[6-chloropyrimidin-4-yloxy]phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 0.22 g (0.00125 mol, having a concentration of 33%) of trimethylamine solution in water were added sequentially into a 500 mL reaction flask, stirred, heated to 80° C. and incubated for 18 h. When the reaction was completed, 100 g of water was added. Layers were separated to obtain 252.74 g of a toluene solution of azoxystrobin, with a content of 41.87% (w/w), which is 95.30% of the theoretical value.

The post-processing was performed as Example 1 to provide 95.13 g of azoxystrobin with a content of 98.11% and a yield of 92.55%.

Example 7

In this example, a trimethylamine solution in water with the amount of 0.5 mol % of methyl (E)-2-[2-[6-chloropyrimidin-4-yloxy] phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 45.12 g (0.375 mol, 99%) of 2-cyanophenol, 20.91 g (0.15 mol, 99%) of potassium carbonate and 0.22 g (0.00125 mol, having a concentration of 33%) of trimethylamine solution in water were added sequentially into a 500 mL reaction flask, stirred, heated to 50° C. and incubated for 20 h. When the reaction was completed, 100 g of water was added. Layers were separated to obtain 261.07 g of a toluene solution of azoxystrobin, with a content of 40.1% (w/w), 96.33% of the theoretical value.

The post-processing was performed as Example 1 to provide 97.2 g of azoxystrobin with a content of 98.1% and a yield of 94.55%.

Example 8

In this example, a trimethylamine solution in methanol with the amount of 8 mol % of methyl (E)-2-[2-[6-chloropyrimidin-4-yloxy] phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 30.08 g (0.25 mol, 99%) of 2-cyanophenol, 34.85 g (0.25 mol, 99%) of potassium carbonate and 3.58 g (0.02 mol, having a concentration of 33%) of trimethylamine solution in methanol were added sequentially into a 500 mL reaction flask, stirred, heated to 120° C. and incubated for 5 h. When the reaction was completed, 100 g of water was added. Layers were separated to obtain 252.29 g of a toluene solution of azoxystrobin, with a content of 40.83% (w/w), which is 97.9% of the theoretical value.

The post-processing was performed as Example 1 to provide 97.45 g of azoxystrobin with a content of 98.2% and a yield of 94.89%.

Example 9

In this example, a trimethylamine solution in methanol with the amount of 8 mol % of methyl (E)-2-[2-[6-chloropyrimidin-4-yloxy]phenyl]-3-methoxyacrylate was used as a catalyst to synthesize azoxystrobin. The specific preparation method was:

150 g of toluene, 80.99 g (0.25 mol, 99%) of methyl (E)-2-[2-[6-chloropyrimidin-4-yloxy]phenyl]-3-methoxyacrylate, 39.11 g (0.325 mol, 99%) of 2-cyanophenol, 69.7 g (0.5 mol, 99%) of potassium carbonate and 3.58 g (0.02 mol, having a concentration of 33%) of trimethylamine solution in methanol were added sequentially into a 500 mL reaction flask, stirred, heated to 100° C. and incubated for 12 h. When the reaction was completed, 100 g of water was added. Layers were separated to obtain 244.19 g of a toluene solution of azoxystrobin, with a content of 41.8% (w/w), which is 98.8% of the theoretical value.

The post-processing was performed as Example 1 to provide 98.31 g of azoxystrobin with a content of 98.23% and a yield of 95.76%.

Comparative Example 1

Azoxystrobin was synthesized in the absence of any catalyst in this example. The specific preparation method was as following:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol and 27.88 g (0.2 mol, 99%) of potassium carbonate were added sequentially into a 500 mL reaction flask, stirred, heated to 80° C. and incubated for 8 h. The reaction was monitored and detected, showing that the conversion rate of the raw material (methyl (E)-2-[2[6-chloropyrimidin-4-yloxy]phenyl]-3-methoxyacrylate) was only about 10%. 100 g of water was added. Layers were separated to obtain 245.38 g of a toluene solution of azoxystrobin. The content was measured to be 3.32% (w/w), which is 8.08% of the theoretical value. No further crystallization process was performed due to the low content.

It can be seen from Examples 1 to 9 that good yields can be achieved by using a trimethylamine solution in water and in methanol and a trimethylamine hydrochloride.

The yield of the toluene solution obtained by the reaction can reach about 95%, even if the amount of catalyst was reduced to 0.5 mol %. The catalytic effect of trimethylamine was significant. A little of product was generated with a yield lower than 10% of the theoretical value in Comparative Example 1, which has the same reaction conditions as Example 5 except that the Comparative Example 1 was performed in the absence of trimethylamine catalyst.

Examples 1, 4 and 5 and Comparative Examples 2 to 7

The catalysts used, the molar ratio of the catalyst to the reactant (E)-2-[2-[6-chloropyrimidin-4-yloxy]phenyl]-3-methoxypropenoate and the temperature of the reactions in Examples 1, 4 and 5 and Comparative Examples 2 to 7 were shown in the following Table 1. Other conditions during the preparation process were the same as Example 1. The yields of the toluene solution of azoxystrobin obtained were shown in the following Table 1.

TABLE 1

| | The names of the catalyst | The amount of the catalyst (mol %) | The temperature of the reaction (° C.) | The yields of the toluene solution of azoxystrobin (%) |
|---|---|---|---|---|
| Comparative Example 2 | N,N,N,N-tetramethylethylenediamine | 8 | 80 | 7.5 |
| Comparative Example 3 | N,N-dimethylpiperazine | 8 | 80 | 18.6 |
| Comparative Example 4 | DMAP | 8 | 80 | 2.0 |
| Comparative Example 5 | N,N-dimethylisopropylamine | 8 | 80 | 8.8 |
| Comparative Example 6 | DBU | 8 | 80 | 8.2 |
| Comparative Example 7 | triethylamine | 8 | 80 | 5.3 |
| Example 1 | trimethylamine solution in water | 8 | 80 | 98.9 |
| Example 4 | trimethylamine solution in methanol | 8 | 80 | 98.5 |
| Example 5 | trimethylamine hydrochloride | 8 | 80 | 98.1 |

It can be seen from Table 1 that the yield of the product azoxystrobin was extremely decreased when replacing the trimethylamine catalyst with a similar basic substance such as triethylamine, DBU, N,N-dimethylisopropylamine, DMAP, N,N-dimethylpiperazine and N,N,N,N-tetramethylethylenediamine under the same conditions. Therefore, the trimethylamine catalyst was specific for the reaction of the present invention and cannot be replaced by other similar basic substances.

Example 10

The trimethylamine catalyst was recycled in this example with the method as following:

(A) Trimethylamine Absorption Test with Water

Approximate 5 kg of water phase, which was obtained according to Example 1, was collected. The water phase was combined and heated to 50° C. with stirring, and then purged with nitrogen to obtain a gas mixture. The gas mixture was subjected to a three-stage absorption with 200 g of water to obtain 239.55 g of a trimethylamine solution in water with a content of 16.13% and a recycling rate of 95.22%.

(B) Trimethylamine Absorption Test with Methanol

Approximate 5 kg of water phase, which was obtained according to Example 1, was collected. The water phase was combined and heated to 50° C. with stirring, and then purged with nitrogen to obtain a gas mixture. The gas mixture was subjected to a three-stage absorption with 200 g of methanol to obtain 238.54 g of a trimethylamine solution in water with a content of 15.84% and a recycling rate of 93.11%.

(C) Trimethylamine Absorption Test with 15% of Dilute Hydrochloric Acid

Trimethylamine was absorbed by using 200 g of hydrochloric acid solution having a concentration of 15% through a three-stage absorption apparatus according to the procedure of Example 8 to obtain 238.87 g of a trimethylamine solution in dilute hydrochloric acid, with a content of 26.51% and a recycling rate of 96.53%.

Example 11

In this example, a recycled trimethylamine solution in water (having a content of 16.13%) was used as a catalyst to synthesize azoxystrobin, the amount of which is 8 mol % of methyl (E)-2-[2-[6-chloropyrimidin-4-yloxy]phenyl]-3-methoxyacrylate. The specific method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 7.33 g (0.02 mol, having a concentration of 16.13%) of the recycled trimethylamine solution in water were added sequentially into a 500 mL reaction flask, stirred, heated to 80° C. and incubated for 8 h. When the reaction was completed, 100 g of water was added. Layers were separated to obtain 253.02 g of a toluene solution of azoxystrobin, with a content of 40.58% (w/w), which is 98.22% of the theoretical value.

The post-processing was performed as Example 1 to provide 97.94 g of azoxystrobin with a content of 98.18% and a yield of 95.35%.

Example 12

In this example, a recycled trimethylamine solution in methanol (having a content of 15.84%) was used as a catalyst to synthesize azoxystrobin, the amount of which is 8 mol % of methyl (E)-2-[2-[6-chloropyrimidin-4-yloxy]phenyl]-3-methoxyacrylate. The specific method was:

150 g of toluene, 80.99 g (0.25 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 7.46 g (0.02 mol, having a concentration of 15.84%) of the recycled trimethylamine solution in methanol were added sequentially into a 500 mL reaction flask, stirred, heated to 80° C. and incubated for 8 h. When the reaction was completed, 100 g of water was added. Layers were separated to obtain 248.38 g of a toluene solution of azoxystrobin, with a content of 41.34% (w/w), which is 98.15% of the theoretical value.

The post-processing was performed as Example 1 to provide 98.34 g of azoxystrobin with a content of 98.31% and a yield of 95.87%.

Example 13

In this example, a recycled trimethylamine hydrochloride solution in water (having a content of 26.51%) was used as a catalyst to synthesize azoxystrobin, the amount of which is 8 mol % of methyl (E)-2-[2-[6-chloropyrimidin-4-yloxy]phenyl]-3-methoxyacrylate. The specific method was:

150 g of toluene, 80.99 g (0.02 mol, 99%) of methyl (E)-2-[2-[6-chloropyrimidin-4-yloxy]phenyl]-3-methoxyacrylate, 33.09 g (0.275 mol, 99%) of 2-cyanophenol, 27.88 g (0.2 mol, 99%) of potassium carbonate and 7.21 g (0.02 mol, having a concentration of 26.51%) of the recycled trimethylamine hydrochloride solution in water were added sequentially into a 500 mL reaction flask, stirred, heated to 80° C. and incubated for 8 h. When the reaction was completed, 100 g of water was added. Layers were separated to obtain 246.64 g of a toluene solution of azoxystrobin, with a content of 41.66% (w/w), which is 98.15% of the theoretical value.

The post-processing was performed as Example 1 to provide 98.14 g of azoxystrobin with a content of 98.28% and a yield of 95.64%.

It can be seen from Examples 11 to 13 that the trimethylamine was recyclable, and the recycled trimethylamine can also be normally used for the synthesis of azoxystrobin, which also has good catalytic efficiency and leading to a good product yield.

The present invention provides a process for preparing azoxystrobin, which is performed by using 0.5 to 15 mol % of trimethylamine catalyst for catalyzing, allowing 2-cyanophenol or a salt thereof to be reacted with a compound represented by formula I in a non-polar inert solvent to obtain azoxystrobin and allowing the yield of the product azoxystrobin to reach 98% or more, the yield of separated product to reach 95% or more and the post-processing to be simple. The trimethylamine catalyst can be recycled and reused in synthesizing the target product azoxystrobin, which not only reduces the cost but also reduces the total nitrogen and COD in wastewater. The advantages regarding of cost and environmental protection in the method according to the present invention are significant and thus the method is suitable for industrial production.

Detailed methods of the present invention are illustrated by the examples described above in the present invention. However, the present invention is not limited to the detailed methods described above, i.e. it does not mean that the present invention must rely on the detailed methods described above to be implemented. Those skilled in the art should understand that any modifications to the present invention, equivalent replacements of each raw material of the present invention, additions of auxiliary components, selections of specific methods and the like fall within the protection scope and the disclosure scope of the present invention.

We claim:

1. A preparation method for azoxystrobin, wherein the preparation method comprises reacting 2-cyanophenol or a salt thereof with a compound represented by formula I under the catalysis of a trimethylamine catalyst to obtain azoxystrobin represented by formula II:

Formula I

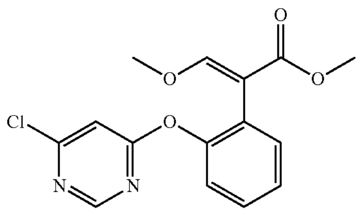

-continued

Formula II

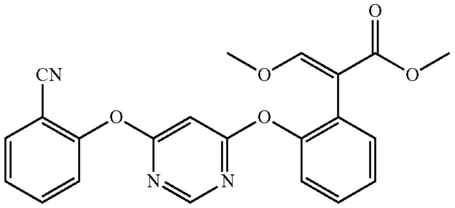

wherein the reaction is performed in the presence of an acid acceptor.

2. The preparation method according to claim 1, wherein the trimethylamine catalyst is trimethylamine, a trimethylamine solution, or a salt of trimethylamine.

3. The preparation method according to claim 2, wherein the trimethylamine solution is any one selected from the group consisting of a trimethylamine solution in water, a trimethylamine solution in methanol, a trimethylamine solution in ethanol, a trimethylamine solution in toluene and a trimethylamine hydrochloride solution, or a combination of at least two selected therefrom.

4. The preparation method according to claim 2, wherein the salt of trimethylamine is any one selected from the group consisting of trimethylamine hydrochloride, trimethylamine sulfate and trimethylamine methanesulfonate, or a combination of at least two selected therefrom.

5. The preparation method according to claim 1, wherein the reaction is performed in a non-polar inert solvent.

6. The preparation method according to claim 5, wherein the non-polar inert solvent is toluene, xylene or butyl acetate.

7. The preparation method according to claim 1, wherein the salt of 2-cyanophenol is potassium 2-cyanophenoxide.

8. The preparation method according to claim 1, wherein the acid acceptor is potassium carbonate and/or sodium carbonate.

9. The preparation method according to claim 1, wherein the amount of the trimethylamine catalyst is 0.5-15 mol % of the compound represented by formula I.

10. The preparation method according to claim 1, wherein the molar ratio of 2-cyanophenol or a salt thereof to the compound represented by formula I is 1:1 to 1.5 to 1.

11. The preparation method according to claim 1, wherein the molar ratio of the acid acceptor to the compound represented by formula I is 0.6:1 to 2:1.

12. The preparation method according to claim 1, wherein the reaction is performed at a temperature of 50-120° C.

13. The preparation method according to claim 1, wherein the reaction is performed for 5-20 h.

14. The preparation method according to claim 1, wherein the preparation method comprises: reacting 2-cyanophenol or a salt thereof with a compound represented by formula I in a non-polar inert solvent at 50-120° C. under the catalysis of a trimethylamine catalyst to obtain the azoxystrobin represented by formula II, in which the amount of the trimethylamine catalyst is 0.5-15 mol % of the compound represented by formula I and the molar ratio of 2-cyanophenol or a salt thereof to the compound represented by the formula I is 1:1 to 1.5:1.

15. The preparation method according to claim 1, wherein the trimethylamine catalyst is recycled trimethylamine.

16. The preparation method according to claim 1 comprising the further step of recycling the trimethylamine catalyst.

* * * * *